(12) United States Patent
Fukatsu et al.

(10) Patent No.: US 8,892,577 B2
(45) Date of Patent: Nov. 18, 2014

(54) APPARATUS AND METHOD FOR STORING MEDICAL INFORMATION

(75) Inventors: Hiroshi Fukatsu, Nagoya (JP); Akira Iwasa, Nasushiobara (JP); Kenichi Niwa, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 167 days.

(21) Appl. No.: 12/032,006

(22) Filed: Feb. 15, 2008

(65) Prior Publication Data

US 2008/0201372 A1 Aug. 21, 2008

(30) Foreign Application Priority Data

Feb. 16, 2007 (JP) ................. 2007-037113

(51) Int. Cl.
*G06F 17/30* (2006.01)
*G06F 19/00* (2011.01)

(52) U.S. Cl.
CPC .................. *G06F 19/321* (2013.01)
USPC ........... 707/754; 707/667; 707/673; 707/748; 707/755

(58) Field of Classification Search
USPC ............ 707/999.101, 999.102, 999.103, 707/999.107, 999.202, 999.203, 999.204, 707/999.205
See application file for complete search history.

(56) References Cited

U.S. PATENT DOCUMENTS

| | | | | |
|---|---|---|---|---|
| 8,023,704 | B2* | 9/2011 | Oosawa | 382/128 |
| 2002/0087503 | A1* | 7/2002 | Judd et al. | 707/1 |
| 2004/0088317 | A1* | 5/2004 | Fabrick et al. | 707/102 |
| 2004/0128164 | A1* | 7/2004 | DeJarnette et al. | 705/2 |
| 2005/0075905 | A1* | 4/2005 | Bennett et al. | 705/2 |
| 2005/0226405 | A1* | 10/2005 | Fukatsu et al. | 380/1 |
| 2006/0184524 | A1* | 8/2006 | Pollanz | 707/6 |
| 2006/0195793 | A1* | 8/2006 | Feihl et al. | 715/751 |
| 2006/0242143 | A1* | 10/2006 | Esham et al. | 707/6 |
| 2007/0106537 | A1* | 5/2007 | Moore | 705/3 |
| 2007/0167713 | A1* | 7/2007 | Fukatsu et al. | 600/407 |
| 2007/0192138 | A1* | 8/2007 | Saito et al. | 705/3 |
| 2007/0271316 | A1* | 11/2007 | Hollebeek | 707/204 |
| 2007/0282629 | A1* | 12/2007 | Plambeck | 705/2 |
| 2008/0133596 | A1* | 6/2008 | Chang | 707/104.1 |
| 2008/0167902 | A1* | 7/2008 | Baba et al. | 705/3 |

FOREIGN PATENT DOCUMENTS

| | | |
|---|---|---|
| JP | 11-235334 | 8/1999 |
| JP | 2005-31740 | 2/2005 |
| JP | 2007-167634 | 7/2007 |

OTHER PUBLICATIONS

U.S. Appl. No. 12/260,395, filed Oct. 29, 2008, Futami, et al.
U.S. Appl. No. 12/100,736, filed Apr. 10, 2008, Matsue, et al.
U.S. Appl. No. 12/107,356, filed Apr. 22, 2008, Kazuno, et al.
U.S. Appl. No. 12/100,780, filed Apr. 10, 2008, Kazuno, et al.

* cited by examiner

*Primary Examiner* — Mohammad S Rostami
(74) *Attorney, Agent, or Firm* — Oblon, Spivak, McClelland, Maier & Neustadt, L.L.P.

(57) ABSTRACT

There are provided an input unit which inputs an object with scan information attached thereto into an image of a subject acquired on the basis of the scan information, and an insertion unit which inserts report information to the object when preparation of an image interpretation report of a study based on the image is completed.

4 Claims, 6 Drawing Sheets

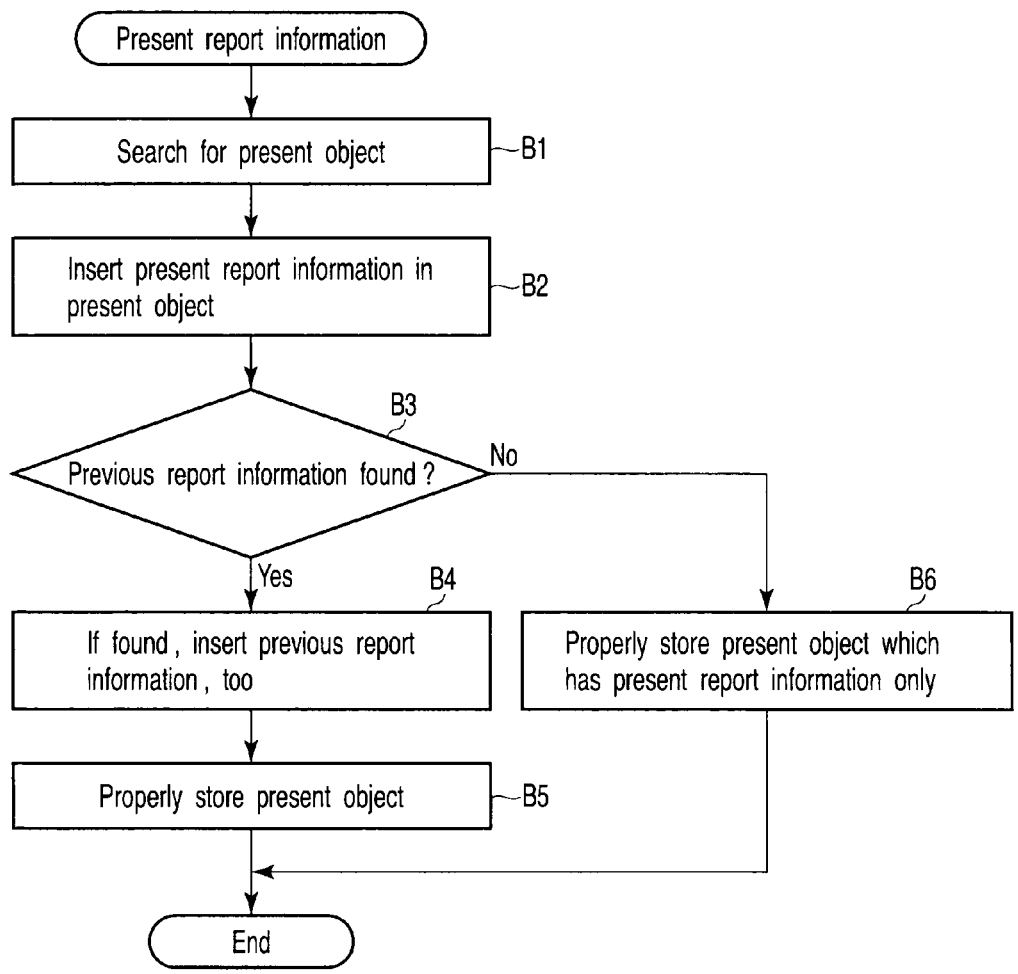
F I G. 4

APPARATUS AND METHOD FOR STORING MEDICAL INFORMATION

CROSS-REFERENCE TO RELATED APPLICATIONS

This application is based upon and claims the benefit of priority from prior Japanese Patent Application No. 2007-037113, filed Feb. 16, 2007, the entire contents of which are incorporated herein by reference.

BACKGROUND OF THE INVENTION

1. Field of the Invention

The present invention relates to an apparatus and method for storing medical information connected to a medical diagnostic imaging apparatus, medical diagnostic imaging workstations, medical diagnostic imaging report preparation support systems, etc. via a network.

2. Description of the Related Art

In recent years, the area of expertise of medical practice has been segmentalized. For example, diagnostic imaging is divided into the acquisition of diagnostic images of a patient, interpretation of radiogram acquired and report preparation, explanation of diagnostic results and therapeutic strategy based on the report results, and other operations. Each operation is taken charge by each specialist (doctor in attendance or engineer in charge), and by all these operations, medical practices such as diagnosis, etc. for a patient are achieved. Each specialist implements each operation by referring to past diagnostic information properly based on information created by other specialists in the operations of the preceding stages. These operations, for example, are conducted by a medical diagnostic imaging apparatus such as an X-ray Computed-Tomographic scanner (X-ray CT scanner) or Magnetic Resonance Imaging apparatus (MRI apparatus) that acquires diagnostic images, a PACS server that stores the diagnostic images in memory, and an image reference apparatus for interpreting the diagnostic images.

FIG. 6 shows one example of flow of a medical practice (request from a patient to image study) in diagnostic imaging. First of all, a requested physician (attending physician) creates a study order on the basis of questions for a patient, etc. and tells a laboratory technician to conduct a study (Step Sa). The order referred to here is a study request which is sent to a variety of medical diagnostic imaging apparatuses using an order system via a network, etc. and which must be done next.

Next, the laboratory technician conducts the study using a predetermined medical diagnostic imaging apparatus and obtains images concerning an area to be treated (Step Sb). This study is conducted by selecting a desired study from the list of study requests (based on the study order) displayed on a monitor of, for example, the medical diagnostic imaging apparatus. Consequently, the study is, in principle, conducted in accordance with the study order. There are, however, cases in which these pieces of information only are not sufficient for determining study methods, photographed range and direction, and imaging conditions. In such cases, the laboratory technician refers to previous study images, previous reports, and key images (images on which the diagnosis is based) related with the previous reports, and conducts the study with consideration given to the imaging range and direction and imaging conditions so as to obtain the same images. The obtained image data is outputted as digital data from the medical diagnostic imaging apparatus and stored, for example, in a PACS server. Note that, in the medical diagnostic imaging apparatus and PACS server, in general, the image is controlled by dividing into a hierarchy of study, series (indices to identify one scan processing), and image. Consequently, in the case where a plurality of pieces of scans are conducted in one study, a plurality of series information that correspond to the study are stored in linkage with one another. In each series, a plurality of images that correspond to the series (that is, the scan processing) are stored in linkage with one another.

Then, an image interpreting physician of Department of Radiology creates an image interpretation report that corresponds to the study order (step Sc). In such event, it becomes important to diagnose by comparing images on which the previous diagnostic imaging is based, that is, key images linked to the previous report, with the present study image. Consequently, the image interpreting physician of Department of Radiology refers to the order and confirms the content of the request, refers to the reports and images of the previous study to confirm the points to be interpreted, and interprets the images of the present study (diagnostic imaging).

Next, the requesting physician refers to the prepared report and judges the diagnostic imaging results (step Sd). That is, the requesting physician interprets the content of the report while referring simultaneously to the key image (diagnosis supporting image) linked to the report, and undertakes diagnostic evaluation integrally with other information not illustrated and conducts treatment.

However, in the conventional medical diagnostic imaging system, there exist the following problems.

In performing comparative diagnosis with past studies, there is a desire to bring the present study content close to the past study content. In the conventional system, the laboratory technician refers to images or film images of past studies stored in a file server and formulates a study plan, or uses information incidental to images of past studies to formulate a study plan. However, the past study images or film images are basically used for image interpretation, and are not intended to be used for reference of the inspection (imaging). Consequently, there are problems that there is an item for which the information necessary for the present study is unable to be thoroughly obtained and which must be established by getting the idea from past images, etc. or imaging conditions which are unable to be set in the same manner as in the previous study emerge. In particular, in cross-sectional images such as MRI images or X-ray CT images, it is difficult for the laboratory technician to grasp information on the imaging position, reconstruction range, etc.

In addition, in general, the patient position and posture on a top panel of a bed frequently differ from those of the previous study because of the conditions at the setting (both of patients and apparatus operators), and there are cases in which the accuracy sufficient for comparative diagnosis cannot be secured only by utilizing the imaging plan (scan range, reconstruction position, etc.) of the previous study.

BRIEF SUMMARY OF THE INVENTION

It is an object of the present invention to provide a technique that can generate high-accuracy reproducible shared information with wide applicability of past medical information and can effectively utilize the relevant shared information.

According to an aspect of the present invention, there is provided an apparatus for storing medical information comprising: a storage unit which stores an object including scan information of a scan executed as study by a medical diagnostic imaging apparatus and a positioning image acquired for the scan; and an insertion unit which inserts information that identifies an interpretation report based on the image obtained by the scan into the object.

According to another aspect of the present invention, there is provided a method for storing medical information, comprising: acquiring an object including scan information of a scan executed as study by a medical diagnostic imaging apparatus and a positioning image acquired for the scan; inserting information that identifies an interpretation report based on the image obtained by the scan into the acquired object; and storing the object with the information that identifies the interpretation report inserted.

BRIEF DESCRIPTION OF THE SEVERAL VIEWS OF THE DRAWING

FIG. 4 shows a processing flow of inserting the present (previous) report information into an object in an apparatus for storing medical information 20, and in particular, is a flow chart showing operation of a present (previous) report information inserting unit 28.

DETAILED DESCRIPTION OF THE INVENTION

Figure 1:
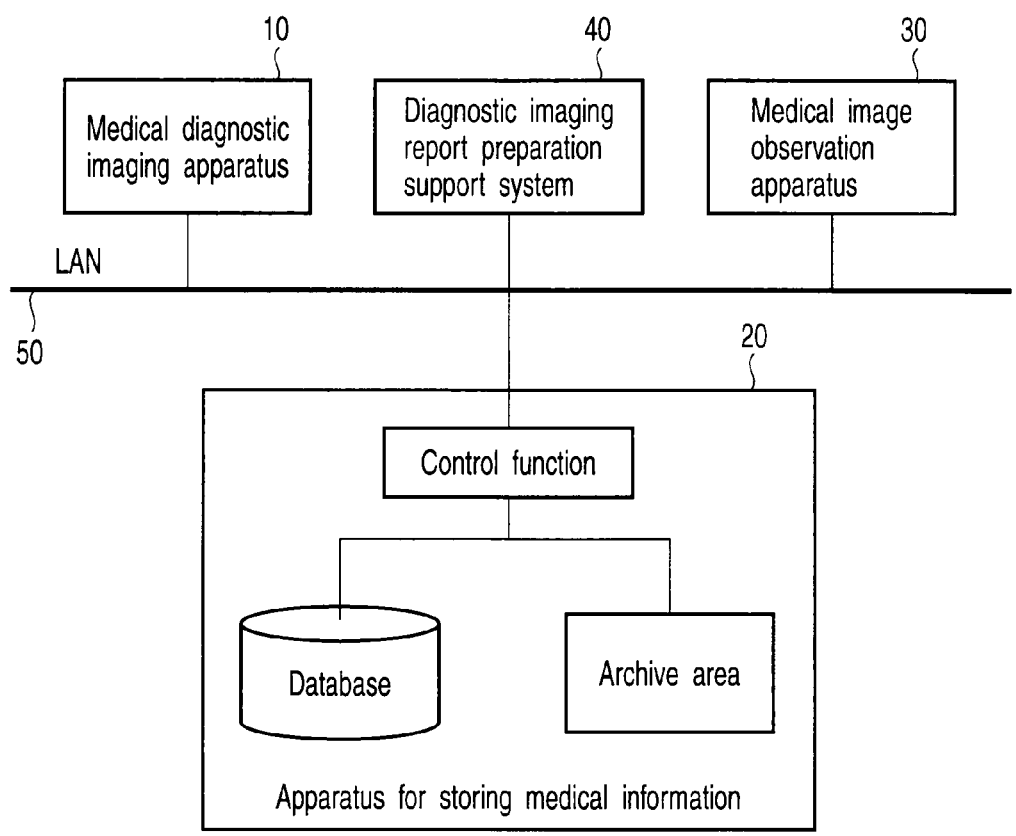
FIG. 1 shows a schematic configuration of a medical diagnostic imaging system including an apparatus for storing medical information according to one embodiment of the present invention.

Referring now to the drawings, embodiments of the present invention will be described.

The inventor of the present invention has made a following proposal in order to create high-accuracy reproducible shared information with wide applicability of past medical information and to effectively utilize the relevant shared information. In this proposal, in a system including a medical diagnostic imaging apparatus, a medical information storage apparatus, a medical diagnostic imaging workstation, and a diagnostic imaging report preparation support system, an object (object) that holds imaging information of the study, key image information, and inspection information referred to at the time of imaging is created and controlled. This object is composed of image information and incidental (character or numerical value) information in order to effectively utilize the information (for example, positioning image, imaging position, imaging range, imaging condition, and image generation condition) used in the medical practice in the past. This object is created, stored, and controlled in respective apparatuses and systems as an entity of information separate from regular image data (for example, files).

Specifically, the object includes image information and at least one incidental information of object-specific information, human body coordinates information, imaging conditions, image generation conditions, and key image information, and such pieces of information are outlined as follows.

(1) Image information: One or more positioning images for referring to the position or range (for example, scout images used for an X-ray CT apparatus, coronal images by pilot scan used in an MRI apparatus, etc.). In this event, the range is a physical range in which a medical imaging diagnostic apparatus actually supplies energy by X-ray, high-frequency, etc., and a detector targets at signal detection or image creation on the basis of the energy supplied.

(2) Object-specific information: This is information to distinguish one object from other objects or to indicate the relevance between one object and other objects. Examples thereof include object identifier (object UID), parent object identifier (parent object UID), relation series identifier (relation series UID), and corresponding series identifier (corresponding series UID).

Note that, data specified by each UID has link added thereto. Accordingly, accessing data at the link destination on the basis of each UID enables quick tracking of a test flow derived from the image group. In addition, the object creation date and creation hour may be included in the object specific information.

(3) Body coordinates information: Unlike a coordinate system (generally, coordinates of each apparatus with an absolute bed position or a relative bed position set as a reference) of an image group acquired by scan, it is the information concerning coordinates (body reference coordinates) with a human body structure on an image set as a reference.

(4) Imaging conditions: The imaging conditions are physical conditions necessary for acquiring physical data, which serves as a basis of image creation, from a patient by an imaging operation. Details of the conditions depend on the type of modality.

For example, the imaging conditions of an X-ray CT apparatus are physical quantities, such as scan start position and range (bed movement amount), KV/mA of an X-ray tube, or a bed movement amount (beam pitch) in one rotation with respect to the total width of an obtained image slice. However, the details of the imaging conditions are not limited to this example. For example, the imaging conditions may be configured to include a subject insertion direction (information as to whether the subject is entered from the head or feet) at the time of inspection, whether or not a contrast medium is administered, dosage thereof, kind of drug, patient body position (lying position or posture on a bed), etc. Furthermore, recently, there is a function to automatically control KV/mA to achieve constant image quality in order to reduce radiation exposure, but in such event, the imaging conditions may be configured to include image noise (SD value), which is a control amount.

In addition, for example, in the case of an MRI apparatus, the imaging conditions may include parameters such as imaging range, patient insertion direction and body position, magnetic field intensity, pulse sequence, type of detection coil, location of detection coil, electrocardiographic synchronization, any sign of respiratory synchronization, presence or absence of bed ventilation, body portion to be primarily imaged, and mounting position.

(5) Image generation conditions: Image generation conditions for reconstructing images from physical data obtained by imaging, and examples thereof include reconstruction range, time phase, image position, direction, thickness, FOV (field of view, enlargement factor), reconstruction function, and other filter processing parameters. In addition, the image generation conditions include conditions used in image processing such as volume rendering and MPR processing, which is executed in various medical diagnostic imaging apparatuses and image reference apparatuses. For example, in the case of MPR processing, reference coordinates, normal vector, slice thickness, range, and others fall under these conditions.

(6) Key image information: Key image information is a component on the PACS side and includes information on the key image position, direction, and image processing set in the image interpreting and image diagnosis stages. The object creating unit of each apparatus recognizes appropriate images as key images at a timing at which a specific image is displayed on a PACS image reference apparatus and designated as a key image or a timing at which pasting operation to a report, linking operation to report sentences (hyper link), etc. are performed. The image reference apparatus searches and identifies the object of a series in which the recognized image is included. The image reference apparatus holds the identifier of the image, for example, SOPInstanceUID of DICOM standard, z-axis coordinate position, or direction at the time of observation, FOV, WW/WL, and other information as key image information. In addition, in the case where MPR is created, the position, direction, and generation conditions of an MPR image, which becomes a key image, may be used in the same manner as is the case of image generation conditions.

By holding the foregoing incidental information as objects, images that can be compared with previous images can be properly taken without omission at the start of study image interpretation. Note that, the object does not necessarily have all the foregoing information. That is, the details of the object may be varied in many ways in accordance with the apparatus used and objectives as long as the information used when past medical practice was implemented could be effectively utilized. For example, the object used for a medical diagnostic imaging apparatus (modality) may be configured with patient ID, position information related to the scan range (reconstruction range), incidental information composed of landmark, and reference image as image information. In addition, the object used for PACS may be configured with patient ID, incidental information composed of key image position information and landmark, and reference image as image information. Furthermore, in the case where specifications which do not need any reference image but use simply past imaging conditions, etc. only are desired, the object should be created in the configuration that consists of only incidental information containing imaging conditions, etc.

However, in the above-mentioned technique, the following issues are generated:

(1) On a diagnostic imaging report preparation support system, a plurality of past reports must be displayed, and it takes time as a system to get ready for searching the target report information; and (2) A need to search previous reports from a plurality of past reports is generated in the diagnostic imaging report preparation support system, and the image reading efficiency is degraded.

Therefore, in the apparatus according to the present embodiment, present report information (hereinafter called the "present report information") is included in the object. Note that, in the object, there are cases in which previous report information (hereinafter called the "previous report information") may be included in addition to the present report information. Thus, when a report for the present study is created, investigating the previous object or utilizing the previous report information of the present object (for example, information that can specify the report uniquely such as report UID, etc. or the previous report information itself) allows the previous report information to be displaced automatically on the diagnostic imaging report creation support system, can reduce the time to get ready for searching the report information, and can provide means to improve the image interpreting efficiency by the object.

Now, this will be specifically described. FIG. 1 shows a block diagram of a medical diagnostic imaging system including a apparatus for storing medical information according to one embodiment of the present invention. The medical diagnostic imaging system according to the present embodiment includes a medical diagnostic imaging apparatus 10, an apparatus for storing medical information 20, a medical image observation apparatus 30, and a diagnostic imaging report preparation support system 40, and each apparatus is connected to each other to be communicable by a LAN 50 (irrespective of wired or wireless, or may be wide-area network or private communication network).

In the medical diagnostic imaging apparatus 10, images for study are taken, and are transmitted to the apparatus for storing medical information 20 in a DICOM format as digital images. The images are referred to at the medical image observation apparatus 30.

The object is configured series by series. As described above, the object includes the imaging range and imaging conditions to reproduce the study, information of past study referred to at the time of imaging and reference image, and is created together with other images at the medical diagnostic imaging apparatus 10 at the study imaging. After creation, they are stored in the apparatus for storing medical information 20 as is the case with other images.

Figure 2:
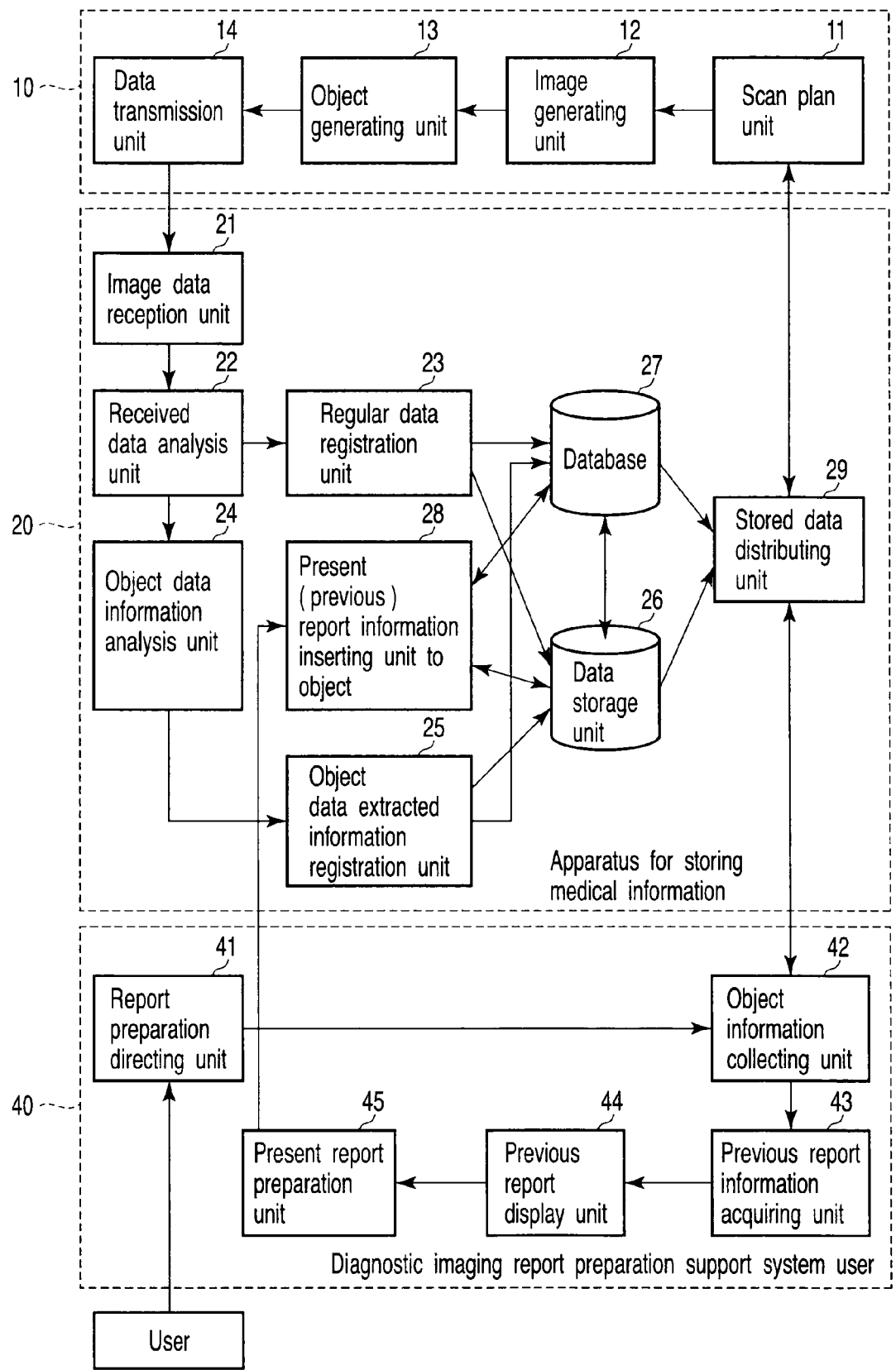
FIG. 2 is a block diagram showing a configuration for inserting report information to an object.

Referring now to FIG. 2, description will be made on the configuration to insert report information to the object. FIG. 2 is a block diagram showing a configuration to insert report information into the object.

The medical diagnostic imaging apparatus 10 includes a scan planning unit 11, an image generating unit 12, an object generating unit 13, and a data transmission unit 14.

The scan planning unit 11 searches for and acquires the object information of past studies of the same patient. Alternatively, it allows the information source to draft a user scan plan and allows it to execute the scan plan.

The image generating unit 12 generates images on the basis of the scan plan.

The object generating unit 13 creates an object as described above including the present imaging conditions, etc. In addition, in the present embodiment, the report information existing in the previous object is inherited and inserted as the previous report information into the object to be newly created. Note that, the report information includes that used for the present scan plan. The image and the information are then given to the data transmission unit 14.

The data transmission unit 14 transmits the given data.

The apparatus for storing medical information 20 includes an image data reception unit 21, a received data analysis unit 22, a regular data registration unit 23, an object data information analysis unit 24, an object data extracted information registration unit 25, a data storage unit 26, a database 27, a present (previous) report information inserting unit 28 to the object, and a stored data distributing unit 29.

The image data reception unit 21 carries out receiving processing of image data transmitted from the data transmission unit 14.

The received data analysis unit 22 determines whether the received data is the object data or regular DICOM data and, if it is the object data, outputs the data to the object data information analysis unit 24, and if the received data is DICOM data, outputs the data to the regular data registration unit 23.

The regular data registration unit 23 registers the image data which is not the object data outputted from the received data analysis unit 22 (that is, DICOM data) to the data storage unit 26 and the database 27.

The object data information analysis unit 24 extracts necessary information (for example, scan information) from the object data outputted from the received data analysis unit 22 and sends the relevant information to the object data extracted information registration unit 25.

The object data extracted information registration unit 25 registers the object data to the data storage unit 26 and registers the information extracted from the object data to the database 27.

The data storage unit 26 writes and stores the data received from the object data extracted information registration unit 25 to an appropriate place. In such event, when a storage place is decided, deleted, or changed, the data storage unit 26 communicates with the database 27 and modifies the database 27. In addition, the data storage unit 26 may be a plurality of HDDs or NASs, etc., and may not be in the apparatus for storing medical information 20 but in another place.

The database 27 controls the information for specifying studies which the database controls, object data information and information for identifying the object data, data storage place, etc.

The present (previous) report information inserting unit 28 to the object adds (inserts) report information to the object when creation of the study image reading report is completed, and delivers the object with the report information inserted to the data storage unit 26. In such event, the present (previous) report information inserting unit 28 also updates the database 27, if the database 27 must be updated.

The stored data distributing unit 29 distributes the object data and image data from the database 27 or data storage unit 26 to a requesting source, such as the scan plan unit 11 or an object information collecting unit 42, in response to the request of the scan plan unit 11 or the object information collecting unit 42. In such event, the image data may be exchanged directly between the data storage unit 26 and the requesting source.

The diagnostic imaging report preparation support system 40 includes a report preparation directing unit 41, the object information collecting unit 42, a previous report information acquiring unit 43, a previous report display unit 44, and a present report preparation unit 45.

The report preparation directing unit 41 gives a report preparation start direction of a designated study to related functions in accordance with a user request.

The object information collecting unit 42 transmits an instruction to display the designated image to an apparatus (not shown) for displaying an image with respect to the designated study and at the same time collects the object related to the image. The object information collecting unit 42 delivers the collected information to the previous report information acquiring unit 43. Note that, the object information collecting unit 42 may be allowed to collect not the object but the information only.

The previous report information acquiring unit 43 analyzes the information collected by the object information collecting unit 42, identifies the previous report information, and delivers the information to the previous report display unit 44. Note that, in the case where there exists the previous report information in the object, that report information should be used. In the case where there is no previous report information in the object, the previous object UID may be inserted in the object or the report information which exists in the object together with StudyInstanceUID may be regarded as the previous report information.

The previous report display unit 44 displays the previous report information delivered from the previous report information acquiring unit 43 on an appropriate place.

The present report preparation unit 45 prompts the user to prepare a report, and when the user finishes preparation of the image reading report of the study, reports the report information prepared recently to the present (previous) report information inserting unit 28.

In a system according to the present embodiment configured as above, discussion will be made on the processing concerning the report information in each system by referring to a flow chart.

Figure 3:
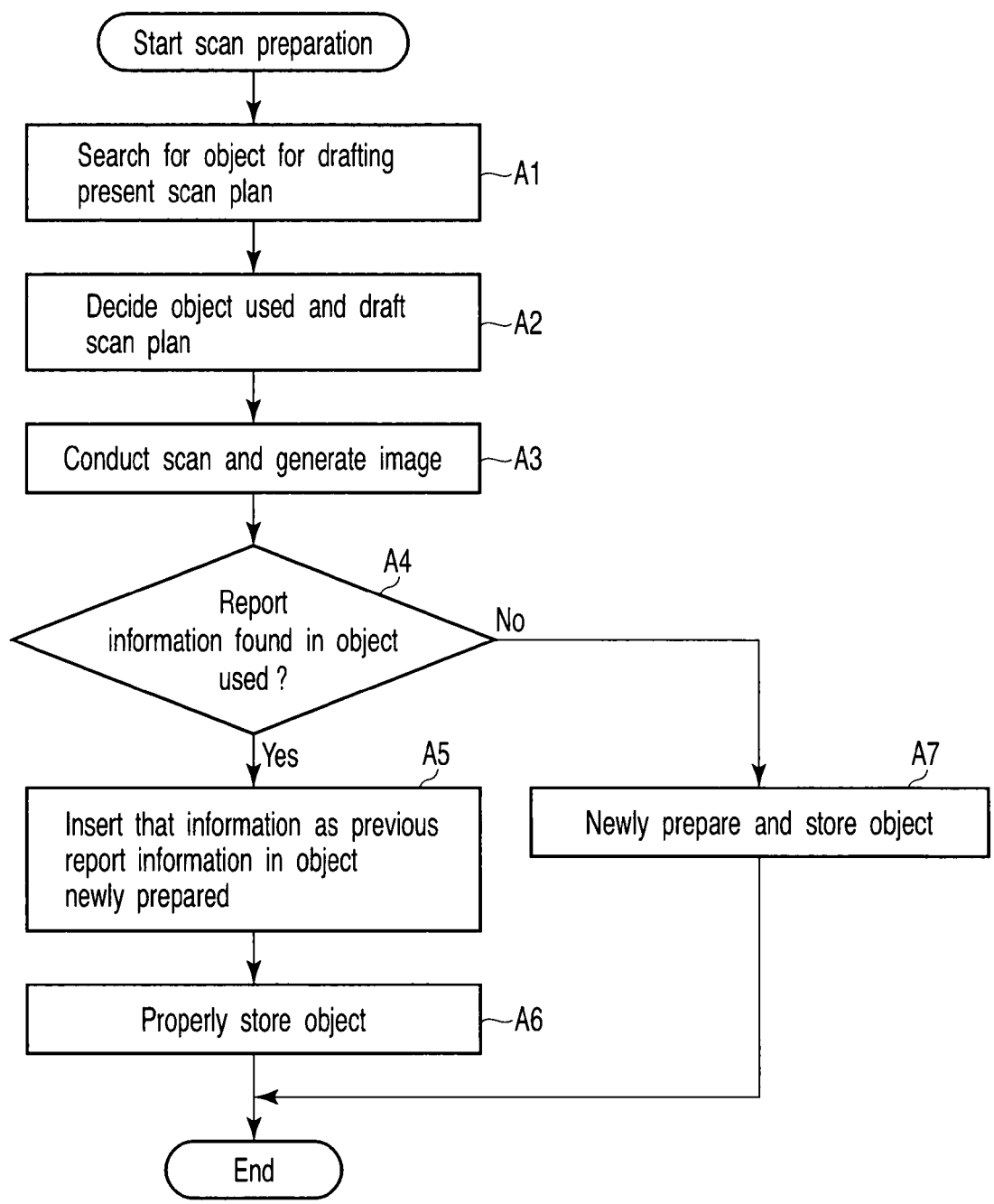
FIG. 3 is a flow chart showing a processing flow to inherit and insert the previous report information into a newly prepared object in a medical diagnostic imaging apparatus 10.

Referring now to FIG. 3, a processing flow of inheriting and inserting the previous report information into the object newly prepared in the medical diagnostic imaging apparatus 10 will be discussed.

The scan plan unit 11 starts scan preparation and searches for an object for drafting a recent scan plan (Step A1). The scan plan unit 11 then decides the object used (as a typical example, the latest object such as previous object, etc.) and drafts a scan plan (Step A2).

The image generating unit 12 scans a subject and generates images (Step A3). The object generating unit 13 determines whether or not the report information has been found in the object used (Step A4), and if there is any report information (Yes in Step A4), inserts the information into the object to be prepared newly as the previous report information (Step A5). In addition, the object generating unit 13 properly stores the object (Step A6).

In addition, if there is no report information in Step A4 (No in Step A4), the object generating unit 13 newly creates and properly stores an object (Step A7). Note that, the object prepared is transmitted to the image data reception unit by the data transmission unit 14.

Referring now to FIG. 4, a processing flow of inserting present (previous) report information into an object in the apparatus for storing medical information 20 will be discussed. FIG. 4 is a diagram showing a processing flow of inserting present (previous) report information into an object in the apparatus for storing medical information 20, and in particular, a flow chart showing operation of the present (previous) report information inserting unit 28.

The present (previous) report information inserting unit 28 searches for an object used at the time of preparing the present report (that is, the present object) (Step B1). The present (previous) report information inserting unit 28 then inserts the present report information into the object (Step B2).

The present (previous) report information inserting unit 28 searches for the present object and past object concerning the relevant patient (for example, previous object, last but one object, etc.) and determines whether or not the previous report information is found (Step B3). In the case where the previous report information is found, the present (previous) report information inserting unit 28 inserts the previous report information (that is, information which enables access to the previous report such as UID for identifying the previous report, previous report location information, etc.) into the object, too (Step B4).

The present (previous) report information inserting unit 28 stores the object in the data storage unit 26 (Step B5). The present (previous) report information inserting unit 28 updates the database 27 as required.

Note that, in the case where no previous report information is found in Step B3 (No in Step B3), the present (previous) report information inserting unit 28 stores the object which has the present report information only in the data storage unit 26 (Step B6). The present (previous) report information inserting unit 28 also updates the database 27 as required.

Figure 5:
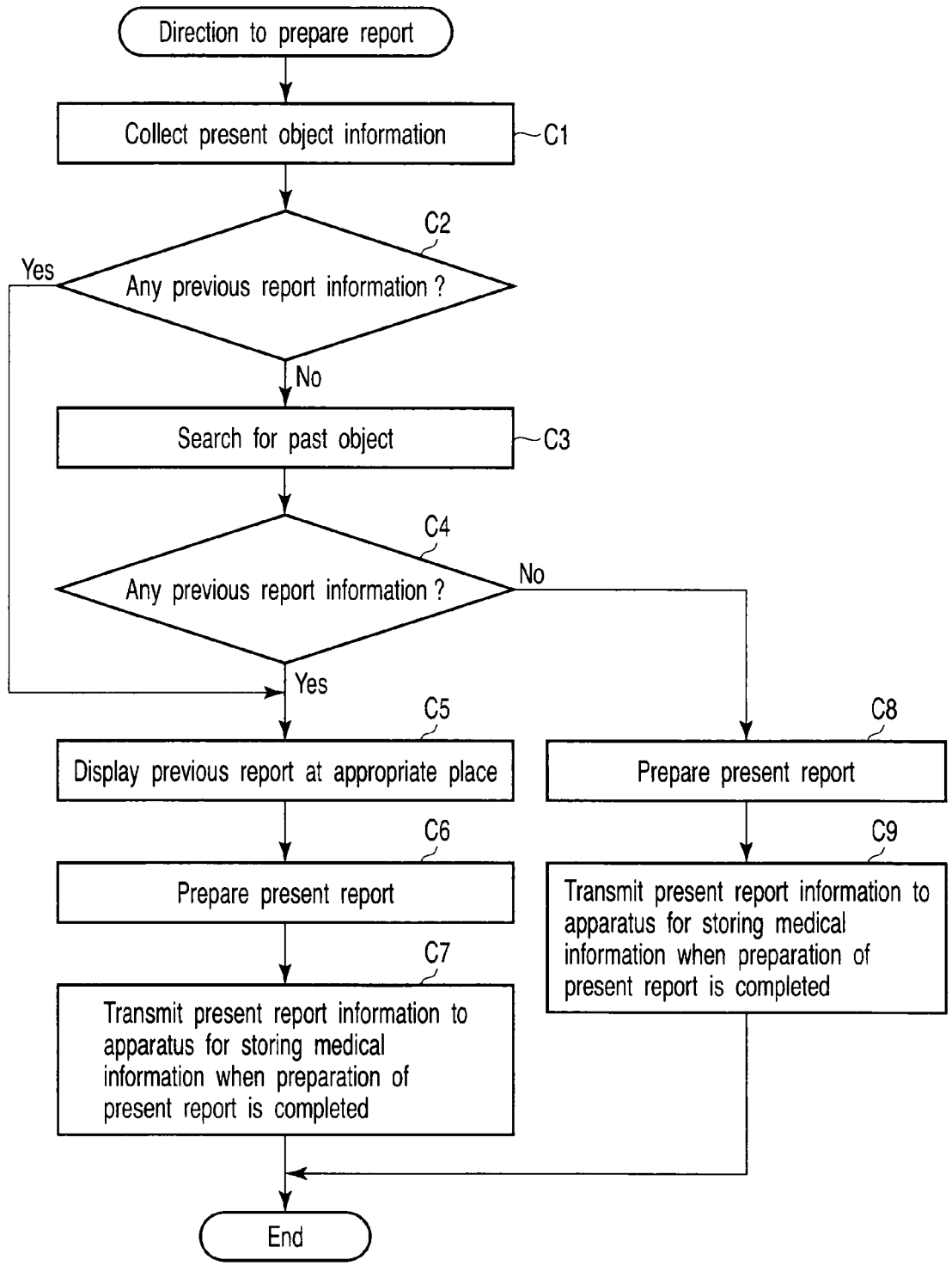
FIG. 5 is a flow chart showing a processing flow of displaying the previous report in a diagnostic imaging report preparation support system 40.
Figure 6:
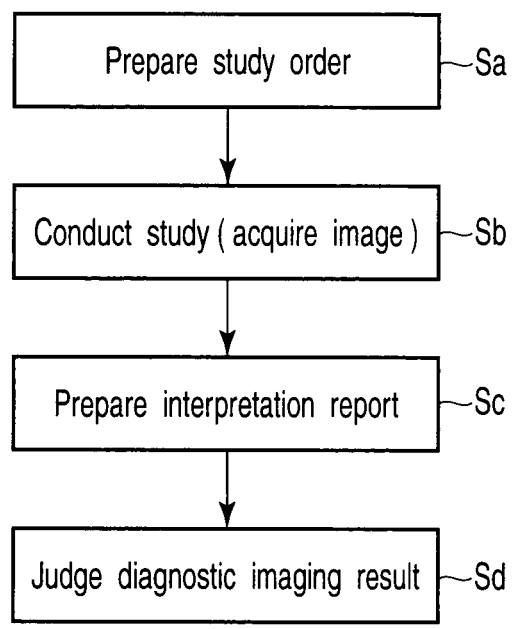
FIG. 6 shows one example of a flow of a medical practice in diagnostic imaging (request from a patient to image study).

Referring now to FIG. 5, discussion will be made on a processing flow of previous report display in the diagnostic imaging report preparation support system 40.

The object information collecting unit 42 collects the present object information (Step C1) and determines whether or not the previous report information exists (Step C2). In the case where it is judged that the previous report information exists in Step C2 (Yes in Step C2), the previous report display unit 44 collects the actual data concerning the previous report on the basis of the relevant previous report information and displays the previous report at an optimum position (Step C5). On the other hand, in the case where it is judged that there is no previous report information in Step C2 (No in Step C2), the object information collecting unit 42 searches for the past objects concerning the relevant patient (Step C3), and determines whether or not the previous report information is found (Step C4).

In Step C4, in the case where there is any previous report information (Yes in Step C4), the previous report display unit 44 collects actual data concerning the previous report on the basis of the relevant previous report information and displays the previous report at an optimum position (Step C5). The present report preparation unit 45 transmits the present report information to the present (previous) report information insertion unit 28 of the apparatus for storing medical information 20 (Step C7) at a point when the user completes preparation of the present report (Step C6).

In Step C4, in the case where there is no previous report information (No in Step C4), the present report preparation unit 45 transmits the present report information to the apparatus for storing medical information (Step C9) at a point when the user completes preparation of the present report (Step C8).

As described above, in the present embodiment, the medical diagnostic imaging system is provided with a function to insert the present report information or previous report information in the object upon completion of the preparation of image interpreting report of the study and a function to automatically check the present or previous object on a list of past reports and display the previous report. Therefore, the previous report information of the present or previous object can be stored and displayed and at the same time the previous report is automatically displayed on the list of past reports. Note that, the object used before may be stored and controlled by preparing an object UID or may be identified by an object used together with StudyInstanceUID.

In addition, in the case where the present study is imaged in the medical diagnostic imaging apparatus 10, a function to inherit the previous report information in the object of the previous study and to create a new object is provided, and the apparatus for storing medical information 20 is provided with a function to control and distribute the information. As a result, the previous report information can be fetched whenever necessary. In addition, in the case where the recent study of a patient who requires follow-up is interpreted, on the medical diagnostic imaging workstation, an image of the previous study to be compared is automatically reproduced on a viewer screen and on a diagnostic imaging report preparation support system screen, an interpretation report of the previous study to be confirmed is automatically reproduced. Therefore, the time and labor to find out comparative subjects can be thereby eliminated.

In addition, in the present embodiment, the previous report information is integrated in the object. Thus, it becomes possible to have the previous report information by the present object alone, and the previous object is no longer required to search for the previous report information. However, it becomes necessary to provide functions to inherit the previous report information in the object of the previous study and to create a new object when the present study is imaged by the medical diagnostic imaging apparatus 10. In addition, the object may be allowed to have both the present report information and the previous report information simultaneously.

The present invention is not limited to the above embodiments and various modifications may be made without departing from the spirit and scope of the invention. In addition, a variety of inventions may be realized by proper combination of a plurality of constituent elements disclosed in the above embodiments.

Even if several constituent elements are omitted from the entire constituent elements explained in the above embodiments, if the problems described in the column of "Problems to be Solved" can be solved and the effects discussed in the "Effect of the Invention" can be obtained, the constitution with these constituent elements omitted can be extracted as inventions.

What is claimed is:

1. A medical information storing apparatus that is connected to a report preparation support system for preparing an interpretation report and stores medical images acquired by a scan executed by a medical diagnostic imaging apparatus, the medical information storing apparatus comprising:
   a storage unit configured to store an object including an imaging condition used for a scan executed by the medical diagnostic imaging apparatus, a positioning image used in the scan in a form of the object linking to a medical image acquired by the scan, and information to identify an imaging range of a past imaging; and
   a report information insertion unit implemented by processing circuitry and configured
      to receive a notice of preparation completion of an interpretation report based on the medical images from a report preparation support system, the medical images being acquired by using the object, at a timing of receiving the notice of preparation completion of the interpretation report,
      to search out the object used in the acquisition of the medical images of the interpretation subject from the storage unit,
      to search a past interpretation report,
      to insert information to specify the interpretation report and the past interpretation report into the searched object in a case where the past interpretation report is found,
      to insert information to specify the interpretation report into the searched object in a case where the past interpretation report is not found, and
      to automatically update the storage unit to store an updated object with the imaging condition, the positioning image, and the information to specify the interpretation report.

2. The apparatus for storing medical information according to claim 1, wherein the report information insertion unit searches for a corresponding object from the image referred to at the time of preparation of a present report from the storage unit and inserts present report information into the object.

3. A method for storing medical information utilizing a medical information storing apparatus that is connected to a report preparation support system for preparing an interpretation report and that stores medical images acquired by a scan executed by a medical diagnostic imaging apparatus, the method comprising:

acquiring an object including an imaging condition used for a scan executed by the medical diagnostic imaging apparatus, a positioning image used in the scan in a form of the object linking to a medical image acquired by the scan, and information to identify an imaging range of a past imaging;

inserting report information by receiving a notice of preparation completion of an interpretation report based the medical images from a report preparation support system, the medical images being acquired by using the object, at a timing of receiving the notice of preparation completion of the interpretation report;

searching out the object used in the acquisition of the medical images of the interpretation subject from the storage unit;

searching a past interpretation report;

inserting information to specify the interpretation report and the past interpretation report into the searched object in a case where the past interpretation report is found;

inserting information to specify the interpretation report into the searched object in a case where the past interpretation report is not found; and automatically updating the storage unit to store an updated object with the imaging condition, the positioning image, and the information to specify the interpretation report.

4. The method for storing medical information according to claim 3, wherein in the insertion, a corresponding object is searched for from the image referred to at the time of preparation of a present report from a plurality of the objects and present report information is inserted into the object.

\* \* \* \* \*